(12) United States Patent
Goshayeshgar

(10) Patent No.: US 9,968,370 B2
(45) Date of Patent: May 15, 2018

(54) MULTI-TINE CUTTING DEVICE

(71) Applicant: Kyphon SÀRL, Neuchatel (CH)

(72) Inventor: Mojan Goshayeshgar, Atherton, CA (US)

(73) Assignee: Kyphon SÀRL, Neuchâtel (CH)

( * ) Notice: Subject to any disclaimer, the term of this patent is extended or adjusted under 35 U.S.C. 154(b) by 1023 days.

(21) Appl. No.: 14/288,508

(22) Filed: May 28, 2014

(65) Prior Publication Data

US 2015/0342628 A1 Dec. 3, 2015

(51) Int. Cl.
*A61B 17/32* (2006.01)
*A61B 17/16* (2006.01)

(52) U.S. Cl.
CPC .... *A61B 17/32002* (2013.01); *A61B 17/1617* (2013.01); *A61B 17/320016* (2013.01); *A61B 2017/320032* (2013.01)

(58) Field of Classification Search
CPC ........ A61B 17/320016; A61B 17/3205; A61B 17/3207; A61B 17/3421; A61B 17/32002; A61B 17/24; A61B 17/28; A61B 17/32; A61B 17/320725; A61B 17/320758; A61B 17/1671; A61B 2017/00349; A61B 2017/00353; A61B 2017/320733; A61B 2017/320064; A61B 10/0275; A61B 10/0266; A61B 2010/0208; A61B 2018/00601
USPC ........ 600/564, 566, 567; 606/170, 171, 167, 606/184, 185, 198
See application file for complete search history.

(56) References Cited

U.S. PATENT DOCUMENTS

| | | |
|---|---|---|
| 4,393,872 A | 7/1983 | Reznik et al. |
| 5,324,284 A | 6/1994 | Imran |
| 5,827,276 A | 10/1998 | LeVeen et al. |
| 5,855,576 A | 1/1999 | LeVeen et al. |
| 5,951,547 A | 9/1999 | Gough et al. |
| 6,425,887 B1 | 7/2002 | McGuckin et al. |
| 6,575,967 B1 | 6/2003 | LeVeen et al. |
| 7,553,307 B2 | 6/2009 | Bleich et al. |
| 7,896,879 B2 | 3/2011 | Solsberg et al. |
| 8,517,934 B2 | 8/2013 | Reznick |
| 8,568,308 B2 | 10/2013 | Reznik |
| 8,632,538 B2 | 1/2014 | Pearson et al. |
| 2006/0235452 A1 | 10/2006 | Schomer et al. |
| 2011/0082387 A1* | 4/2011 | Miller .................. A61B 10/025 600/567 |
| 2014/0018674 A1 | 1/2014 | Solsberg et al. |

(Continued)

*Primary Examiner* — Kathleen Holwerda
*Assistant Examiner* — Socrates L Boutsikaris

(57) ABSTRACT

A cutting device is provided that includes an outer tube. The outer tube includes an inner surface defining a passageway. An inner tube is movably disposed in the passageway such that a distal end of the inner tube extends beyond a distal end of the outer tube. The distal end of the inner tube includes a first cutting element. An inner surface of the inner tube defines a lumen. A shaft is slidably disposed in the lumen. The shaft has a distal end including a second cutting element. A deployment mechanism is coupled to a proximal end of the outer tube. The deployment mechanism includes a body, a push button disposed within the body and a collar disposed about the body. The shaft is fixed relative to the collar and the inner tube is fixed relative to the push button. Systems and methods are disclosed.

20 Claims, 11 Drawing Sheets

(56) References Cited

U.S. PATENT DOCUMENTS

2014/0213931 A1* 7/2014 Lee .................... A61B 10/0233
600/567

* cited by examiner

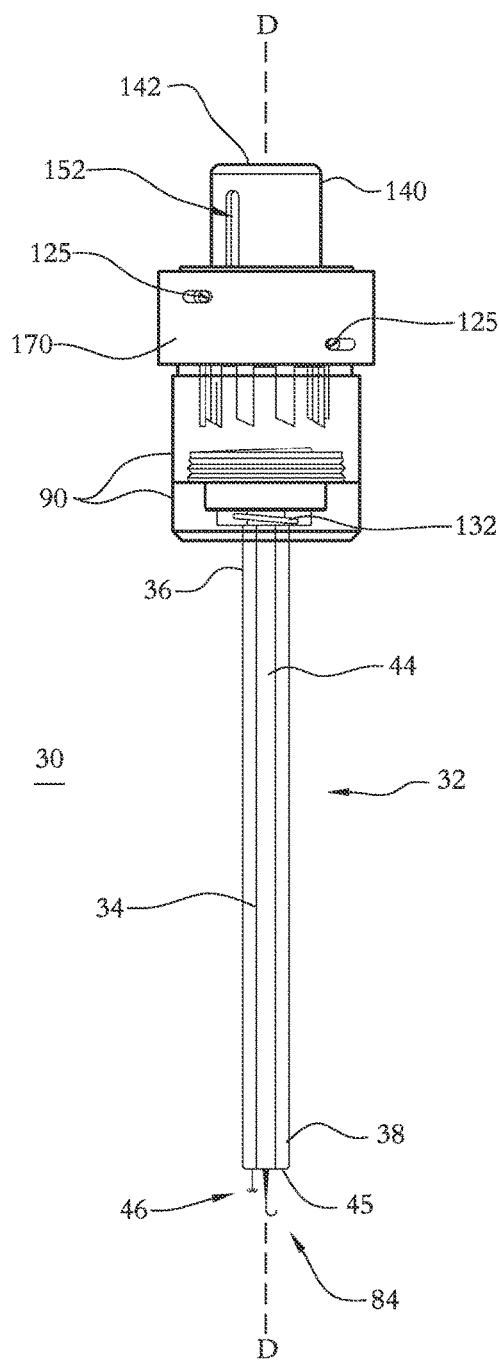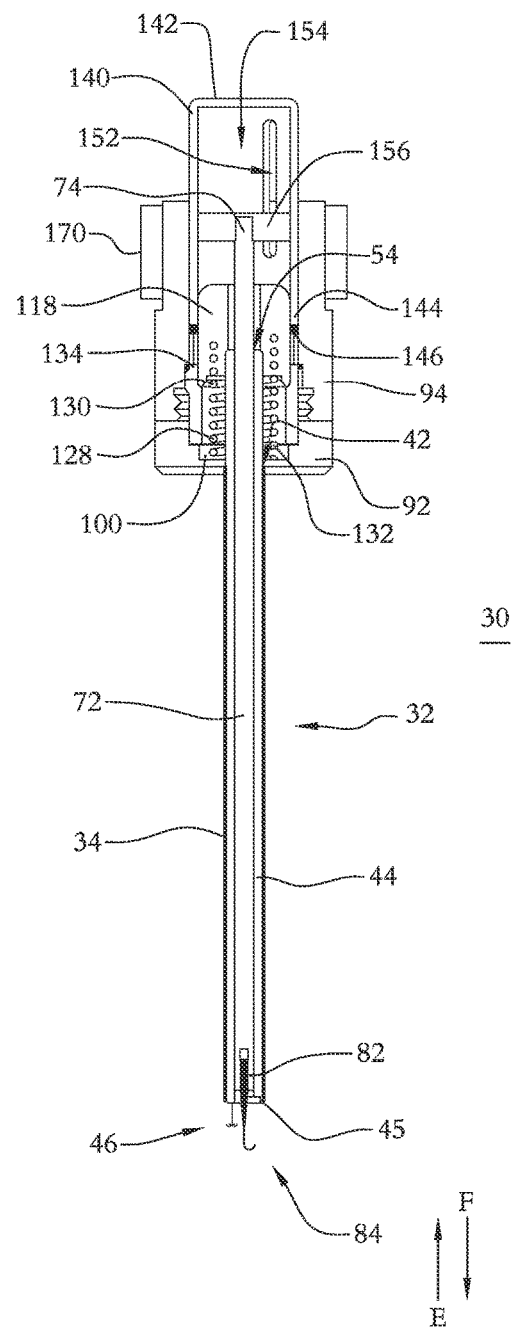
FIG. 1
FIG. 2

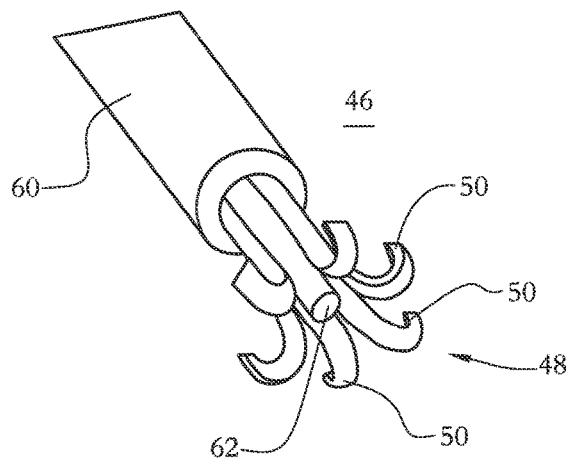
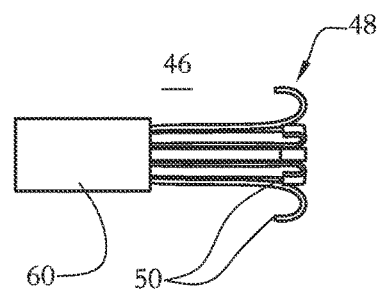
FIG. 9    FIG. 10
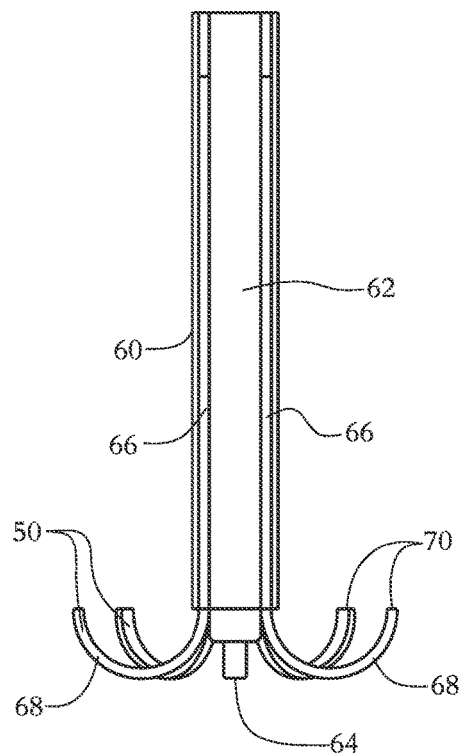
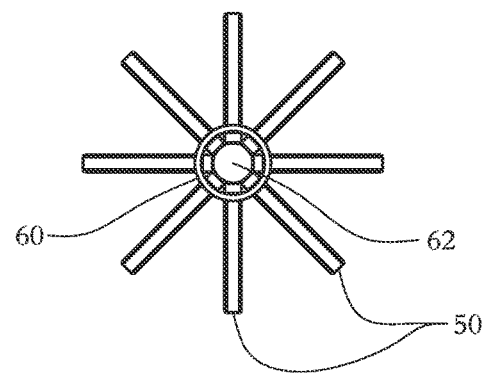
FIG. 11    FIG. 12

MULTI-TINE CUTTING DEVICE

TECHNICAL FIELD

The present disclosure generally relates to medical devices to dissect and evacuate tissue, and more particularly to a surgical system and method employing a retractable device for treatment of hypertrophied ligamentum flavum.

BACKGROUND

Spinal stenosis typically occurs when the spinal cord, cauda equina and/or nerve root(s) are impinged by one or more tissues in the spine, such as a buckled or thickened ligamentum flavum. Impingement of neural and/or neurovascular tissue in the spine by a buckled or thickened ligamentum flavum may cause pain, numbness and/or loss of strength or mobility in one or both of a patient's lower limbs and/or of the patient's back.

In lumbar spinal stenosis (LSS), the space around the spinal cord becomes narrow, thus compressing the spinal cord and the nerve roots. This causes back pain with neurogenic claudication, i.e., pain, numbness, or weakness in the legs that worsens with standing or walking and is alleviated with sitting or leaning forward. Compression of neural elements generally occurs as a result of hypertrophied facet or ligamentum flavum hypertrophy. LSS is one of the most common reasons for back surgery and the most common reason for lumbar spine surgery in adults over 65 years of age. Patients suffering from spinal stenosis are typically first treated with conservative approaches such as exercise therapy, analgesics, anti-inflammatory medications, and epidural steroid injections. When these conservative treatment options fail and symptoms are severe, surgery may be required to remove impinging tissue and decompress the impinged nerve tissue.

The source of most cases of lumbar spinal stenosis is thickening of the ligamentum flavum. Spinal stenosis may also be caused by subluxation, facet joint hypertrophy, osteophyte formation, underdevelopment of spinal canal, spondylosis deformans, degenerative intervertebral discs, degenerative spondylolisthesis, degenerative arthritis, ossification of the vertebral accessory ligaments and the like. A less common cause of spinal stenosis, which usually affects patients with morbid obesity or patients on oral corticosteroids, is excess fat in the epidural space. The excessive epidural fat compresses the dural sac, nerve roots and blood vessels contained therein and resulting in back and leg pain and weakness and numbness of the legs. Spinal stenosis may also affect the cervical and, less commonly, the thoracic spine.

Patients suffering from spinal stenosis are typically first treated with exercise therapy, analgesics and anti-inflammatory medications. These conservative treatment options frequently fail. If symptoms are severe, surgery is required to decompress the canal and nerve roots.

To correct stenosis in the lumbar region, an incision is made in the back and the muscles and supporting structures are stripped away from the spine, exposing the posterior aspect of the vertebral column. The thickened ligamentum flavum is then exposed by removal of the bony arch (lamina) covering the back of the spinal canal (laminectomy). The thickened ligament can then be excised with sharp dissection with a scalpel or punching instruments such as a Kerison punch that is used to remove small chips of tissue. The procedure is performed under general anesthesia. Patients are usually admitted to the hospital for approximately five to seven days depending on the age and overall condition of the patient. Patients usually require between six weeks and three months to recover from the procedure. Many patients need extended therapy at a rehabilitation facility to regain enough mobility to live independently.

Much of the pain and disability after an open laminectomy is due to the tearing and cutting of the back muscles, blood vessels and supporting ligaments and nerves that occurs during the exposure of the spinal column. Also, because these spine stabilizing back muscles and ligaments are stripped and cut off, the spine these patients frequently develop spinal instability post-operatively.

Minimally invasive techniques result in less post-operative pain and faster recovery compared to traditional open surgery. Percutaneous interventional spinal procedures can be performed with local anesthesia, thereby sparing the patient the risks and recovery time required with general anesthesia. Another advantage is that there is less damage to the paraspinal muscles and ligaments with minimally invasive techniques reducing pain and preserving these important stabilizing structures.

Various techniques for minimally invasive treatment of the spine are known. Microdiscectomy is performed by making a small incision in the skin and deep tissues to create a portal to the spine. A microscope is then used to aid in the dissection of the adjacent structures prior to discectomy. The recovery period for this procedure is much shorter than traditional open discectomies. Percutaneous discectomy devices with fluoroscopic guidance have been used successfully to treat disorders of the disc, but not to treat spinal stenosis or the ligamentum flavum directly. Arthroscopy or direct visualization of the spinal structures using a catheter or optical system have also been proposed to treat disorders of the spine, including spinal stenosis. However, these devices still use miniaturized standard surgical instruments and direct visualization of the spine, similar to open surgical procedures. These devices and techniques are limited by the small size of the canal and these operations are difficult to perform and master. Also, these procedures are painful and often require general anesthesia. The arthroscopy procedures are time consuming and the fiber optic systems are expensive to purchase and maintain. In addition, because the nerves of the spine pass through the core of the spine directly in front of the ligamentum flavum, any surgery, regardless of whether is open or percutaneous, includes a risk of damage to those nerves.

It is desirable to provide a method and device for treating spinal stenosis and other spinal disorders without requiring open surgery. It is further desired to provide a system that protects the thecal sac or dura containing the spinal nerves while the ligamentum flavum is cut. Accordingly, there is a need for devices and methods to provide efficient severing or cutting of tissue that can be used during a minimally invasive procedure and/or during an open surgical procedure, such as, for example, open decompression.

SUMMARY

In one embodiment, in accordance with the principle so the present disclosure, a cutting device includes an outer tube extending along a longitudinal axis between a proximal end and a distal end. The outer tube comprises an inner surface defining a passageway. An inner tube is rotatably disposed in the passageway such that a distal end of the inner tube extends beyond the distal end of the outer tube. The distal end of the inner tube comprises a first cutting element. An inner surface of the inner tube defines a lumen. A shaft is slidably disposed in the lumen. The shaft comprises a distal end including a second cutting element. A deployment mechanism is coupled to the proximal end of the outer tube. The deployment mechanism comprises a body, a push button disposed within the body and a collar disposed about the body. The shaft is fixed relative to the collar and the inner tube is fixed relative to the push button.

BRIEF DESCRIPTION OF THE DRAWINGS

The present disclosure will become more readily apparent from the specific description accompanied by the following drawings, in which:

FIG. 1 is a side view, in part phantom, of components of a surgical system in accordance with the principles of the present disclosure;

FIG. 2 is a side, cross sectional view of components shown in FIG. 1;

FIG. 9 is a perspective view of a component shown in FIG. 1;

FIG. 10 is a side view of a component shown in FIG. 1;

FIG. 11 is a side, cross sectional view of a component shown in FIG. 1;

FIG. 12 is a top, cross sectional view of a component shown in FIG. 1;

Like reference numerals indicate similar parts throughout the figures.

DETAILED DESCRIPTION

Figure 3:
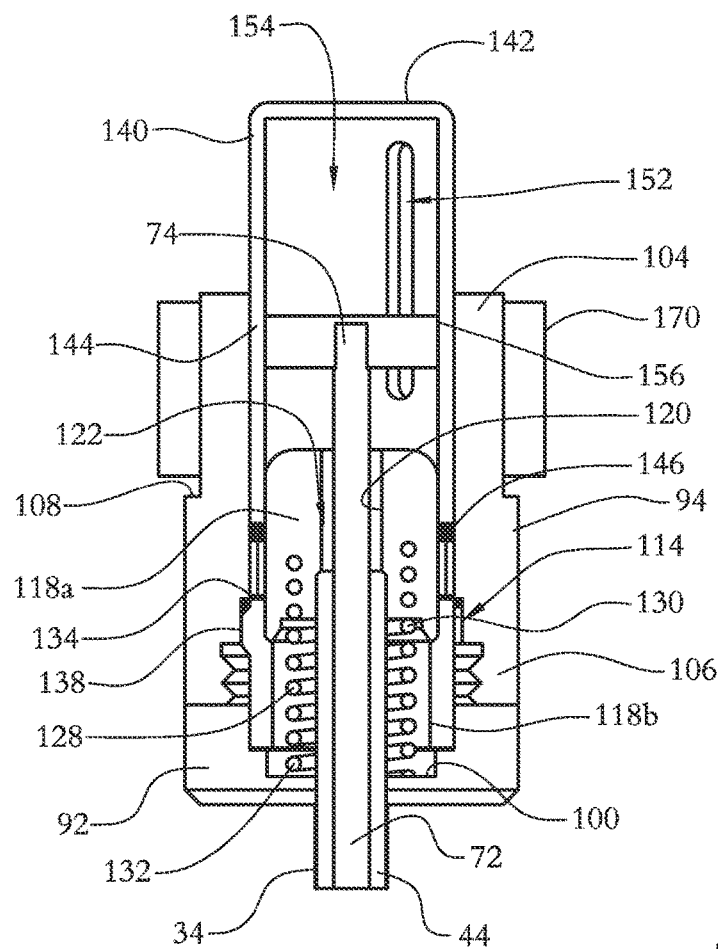
FIG. 3 is a side, cross sectional view of components shown in FIG. 1.
Figure 4:
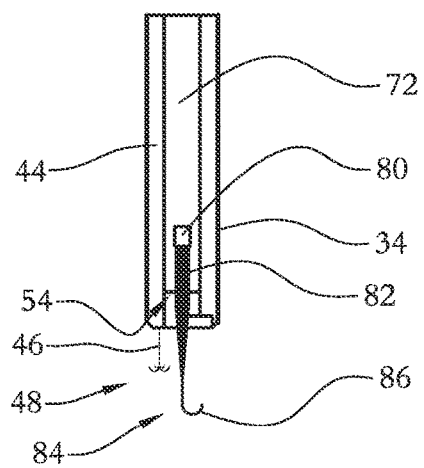
FIG. 4 is a side, cross sectional view of components shown in FIG. 1.

The exemplary embodiments of a surgical system 30 and related methods of use disclosed are discussed in terms of medical devices for the treatment of musculoskeletal disorders, and more particularly, in terms of a surgical system and method for cutting through soft tissues.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a percutaneous approach which removes just enough tissue (lamina or ligamentum flavum) to be effective is provided.

In one embodiment, a device having a retractable ball-point pen-like mechanism is provided to dissect and evacuate the hypertrophied ligamentum flavum in Lumbar Spinal Stenosis. In one embodiment, the device includes an anchor hook. The anchor hook is a central hook to anchor and pull on ligamentum flavum (LF) to increase a potential epidural space. In one embodiment, a suture anchor mechanism can also be utilized. The anchor hook evacuates the dissected LF tissue into a barrel or cannula. An orbiting hook is deployed a distance not further than anchor hook. The orbiting hook is deployed with a deployment mechanism similar to that of a retractable ballpoint pen-like mechanism. An atraumatic tip of the orbiting hook will pass through the ligamentum flavum. An inner cutting edge of the orbiting hook will cut through ligamentum flavum fibers as the inner cutting edge retracts into the barrel. 6 to 20 consecutive deployments of the orbiting hook may be required to dissect the ligamentum flavum by making an annular cut. Upon completion of the annular cut, the anchor hook will evacuate the dissected ligamentum flavum into the barrel.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, hooks and/or tines that are preformed to have different sizes and shapes.

The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference.

The components of system 30, individually or collectively, may also be fabricated from a heterogeneous material such as a combination of two or more of the above-described materials. The components of system 30 may be monolithically formed, integrally connected or include fastening elements and/or instruments, as described herein.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-28, there are illustrated components of the system for performing a surgical procedure in accordance with the principles of the present disclosure.

Figure 6:
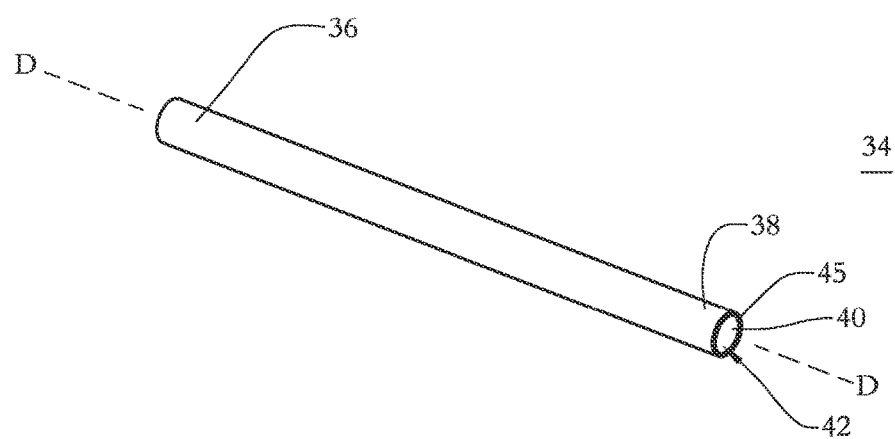
FIG. 6 is perspective view of a component shown in FIG. 1.
Figure 7:
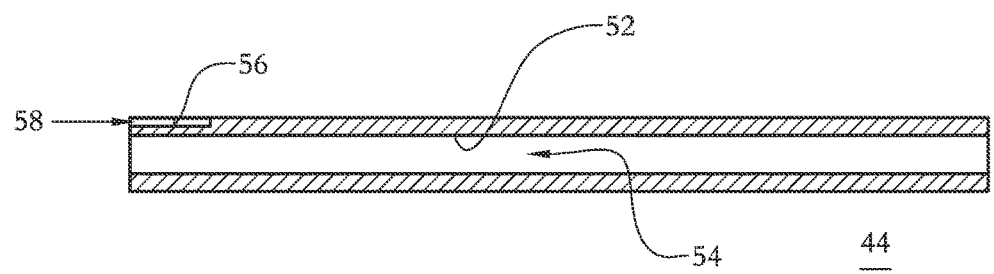
FIG. 7 is a side, cross sectional view of a component shown in FIG. 1.
Figure 8:
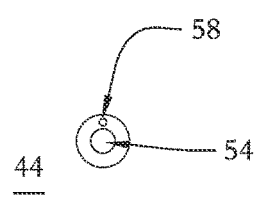
FIG. 8 is an end view of a component shown in FIG. 1.

System 30 includes a surgical instrument, such as, for example a multi-tine cutting device 32. Device 32 comprises an extension tube, such as, for example, an outer tube 34 extending along a longitudinal axis D between a proximal end 36 and a distal end 38. Tube 34 comprises an inner surface 40 defining a passageway 42 having a cylindrical cross sectional configuration and a uniform width along the entire length of tube 34, as shown in FIG. 6, for example. Ends 36, 38 each include an opening that is in communication with passageway 42 such that an item may be inserted into the opening in end 36, translate along axis D through passageway and exit tube 34 through the opening in end 38. In some embodiments, passageway 42 may have various cross section configurations, such as, for example, oval, oblong, triangular, rectangular, square, polygonal, irregular, uniform, non-uniform, variable, tubular and/or tapered. In some embodiments, tube 34 comprises a flexible material configured to allow tube 34 to bend at least slightly without breaking. In some embodiments, tube 34 comprises a rigid material that prevents tube 34 from bending without breaking.

Device 32 comprises an inner tube 44 disposed in passageway 42 such that a distal end 46 of tube 44 extends beyond end 38 for positioning outside of passageway 42. Tube 44 is movably disposed in passageway 42 such that tube 44 is rotatable within passageway 42 about axis D and is translatable within passageway 42 along axis D. End 46 is defined by a cutting element 48, best shown in FIGS. 7-12.

Cutting element 48 comprises a plurality of tines 50 that are spaced apart from one another. In some embodiments, cutting element 48 is offset from a longitudinal axis defined by tube 44 such that cutting element 48 is offset from axis D when tube 44 is positioned within passageway 42. Tube 44 comprises an inner surface 52 defining a lumen 54 having a cylindrical cross sectional configuration that is coaxial with the longitudinal axis defined by tube 44 such that lumen 54 is coaxial with passageway 42 when tube 44 is disposed within passageway 42. In some embodiments, lumen may have various cross section configurations, such as, for example, oval, oblong, triangular, rectangular, square, polygonal, irregular, uniform, non-uniform, variable, tubular and/or tapered.

In some embodiments, cutting element 48 is integrally and/or monolithically formed with tube 44. In some embodiments, tube 44 includes an inner surface 56 defining a cavity 58 having a shaft 60 of cutting element 48 positioned therein such that shaft 60 is fixed relative to tube 44. Cavity 58 has a cylindrical cross sectional configuration. Shaft 60 extends parallel to axis D. Shaft 60 is offset from axis D when tube 44 is positioned within passageway 42. In some embodiments, shaft 60 can be variously connected with cavity 48, such as, for example, monolithic, integral connection, frictional engagement, threaded engagement, mutual grooves, screws, adhesive, nails, barbs and/or raised element. In some embodiments, shaft 60 is removably positioned in cavity 48 and system 30 comprises a plurality of cutting elements 48 each having a different configuration such that a selected cutting element 48 may be positioned within cavity 48. For example, system 30 may include a plurality of cutting elements 48 each having a different number of tines, a different maximum width, etc. In some embodiments, cavity 58 may have various cross section configurations, such as, for example, oval, oblong, triangular, rectangular, square, polygonal, irregular, uniform, non-uniform, variable, tubular and/or tapered.

In some embodiments, tines 50 are disposed radially about a stylet 62 such that tines 50 define a tine arrangement. In some embodiments, tines 50 are evenly spaced apart from one another. In some embodiments, cutting element 48 includes six tines 50 that are spaced apart from one another at a 60 degree angle. In some embodiments, cutting element 48 includes eight tines 50 that are spaced apart from one another at a 45 degree angle. In some embodiments, tines 46 are disposed about stylet 62 in a non-uniform manner such that one set of adjacent tines 50 are spaced apart an angle that is different from an angle in which another set of adjacent tines 50 are spaced apart. In some embodiments, a distal end 64 of stylet 62 protrudes distally from a center of the tine arrangement, as shown in FIGS. 9 and 11, for example. In some embodiments, end 64 comprises a sharp and/or pointed tip configured to penetrate tissue. In some embodiments, end 64 comprises a planar or blunt tip configured to engage tissue, without penetrating tissue. In some embodiments, cutting element 48 may include two or more tines 50. In some embodiments, each of tines 50 is identical. In some embodiments, at least one of tines 50 has a different size or shape than at least one of the other tines 50. In some embodiments, tines 50 are each made of a metal alloy, such as, for example, nitinol. In some embodiments, tines 50 are formed entirely from nitinol.

In some embodiments, as shown in FIG. 11, for example, tines 50 each include a portion 66 that extends parallel to axis D and/or shaft 60 and an arcuate portion 68 extending transverse to axis D and/or shaft 60 having a continuous radius of curvature. End surfaces 70 of portions 68 face away from end 64. Inner surfaces of each tine 50 engage an outer surface of stylet 62 to couple tines 50 with stylet 62, as shown in FIG. 11. Shaft 60 is positioned over portions 66 such that an inner surface of shaft 60 engages outer surfaces of tines 50 to position portions 66 between shaft 60 and stylet 62 to fix tines 50 relative to stylet 62. In some embodiments, tines 50 can be variously connected with stylet 62, such as, for example, monolithic, integral connection, frictional engagement, threaded engagement, mutual grooves, screws, adhesive, nails, barbs and/or raised element.

Figure 13:
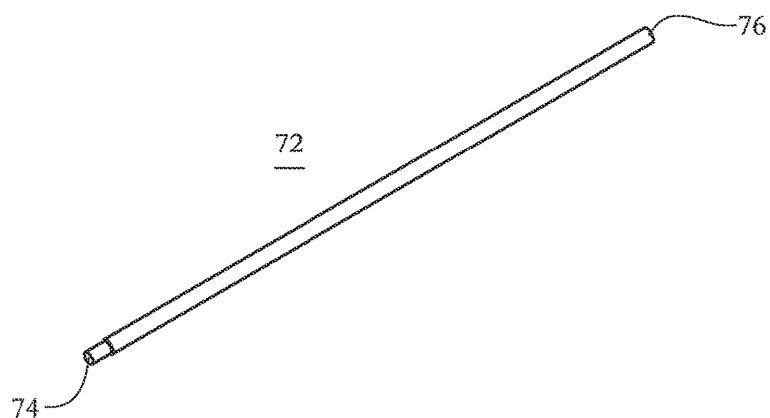
FIG. 13 is perspective view of a component shown in FIG. 1.
Figure 14:
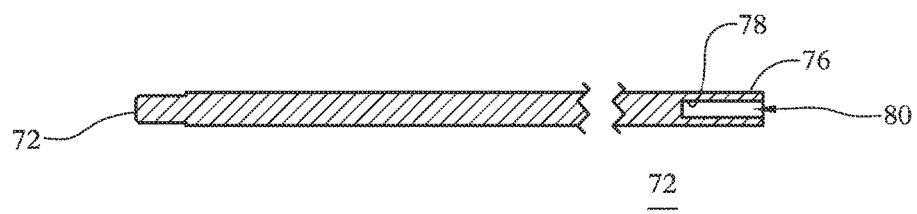
FIG. 14 is a side, cross sectional view of a component shown in FIG. 1.

A stationary rod, such as, for example, shaft 72 is slidably disposed in lumen 54. Shaft 72 comprises a threaded proximal end 74 and a distal end 76 comprising an inner surface 78 defining an aperture 80 having a cylindrical cross sectional configuration, as shown in FIGS. 13 and 14. A shaft 82 of a cutting element 84 is disposed in aperture 80 such that shaft 82 is fixed relative to aperture 80. Cutting element 84 includes a single hook 86. In some embodiments, shaft 82 can be variously connected with aperture 80, such as, for example, monolithic, integral connection, frictional engagement, threaded engagement, mutual grooves, screws, adhesive, nails, barbs and/or raised element. In some embodiments, shaft 82 is removably positioned in aperture 80 and system 30 comprises a plurality of cutting elements 84 each having a different configuration such that a selected cutting element 84 may be positioned in aperture 80. For example, system 30 may include a plurality of cutting elements 84 each having a different number of hooks, different size hooks, a different maximum width, etc. In some embodiments, aperture 80 may have various cross section configurations, such as, for example, oval, oblong, triangular, rectangular, square, polygonal, irregular, uniform, non-uniform, variable, tubular and/or tapered.

Figures 15, 16:
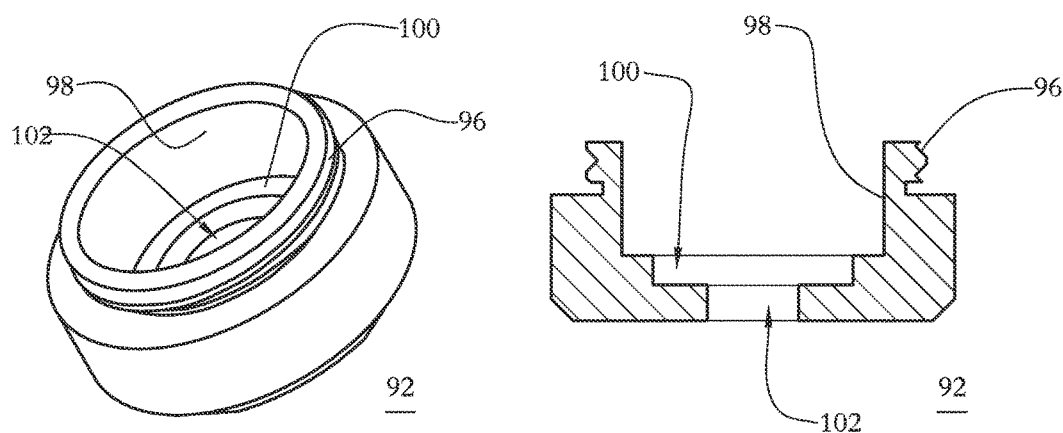
FIG. 15 is a perspective view of a component shown in FIG. 1.
FIG. 16 is a cross sectional view of a component shown in FIG. 1.

Device 32 comprises a deployment mechanism 88 coupled to end 36. Mechanism 88 comprises a body 90 including a retainer nut, such as, for example, a portion 92 and a stationary spline, such as, for example, a portion 94 that is removable from portion 92. Portion 92 comprises a threaded proximal end 96 and an inner surface defining a seat recess 100 and a throughhole 102 distal to seat recess 100, as shown in FIGS. 15 and 16. Tube 34 extends through throughhole 102. In some embodiments, an outer surface of tube 34 engages surface 98 to fix tube 34 relative to portion 92.

Portion 94 comprises a proximal end 104 having a first diameter and a distal end 106 having a second diameter that is greater than the first diameter, as shown in FIGS. 17-21. An interface between ends 104, 106 defines a ledge 108. An inner surface 110 of portion 94 comprises an internal thread form 112 at end 106. Surface 110 comprises a plurality of spaced apart grooves 114 positioned between ends 104, 106. Grooves 114 each extend parallel to a longitudinal axis defined by portion 94. Thread form 112 engages threads on end 96 to couple portion 92 with portion 94, as shown in FIGS. 1-3. Surface 110 defines a conduit 116. Portion 94 comprises openings at ends 104, 106 that are in communication with conduit 116 such that an item may be passed through the opening in end 104, through conduit 116, into portion 92 and exit portion 92 through throughhole 102. In some embodiments, grooves 114 each have the same length to prevent locking of tube 44 relative to body 90 and/or shaft 72 relative to body 90.

Figure 17:
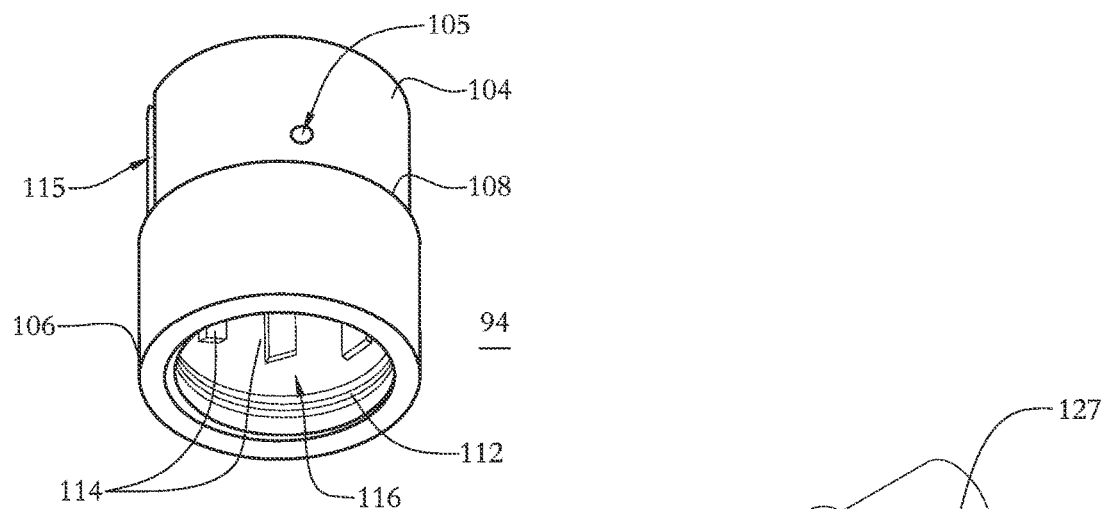
FIG. 17 is a perspective view of a component shown in FIG. 1.
Figure 17A:
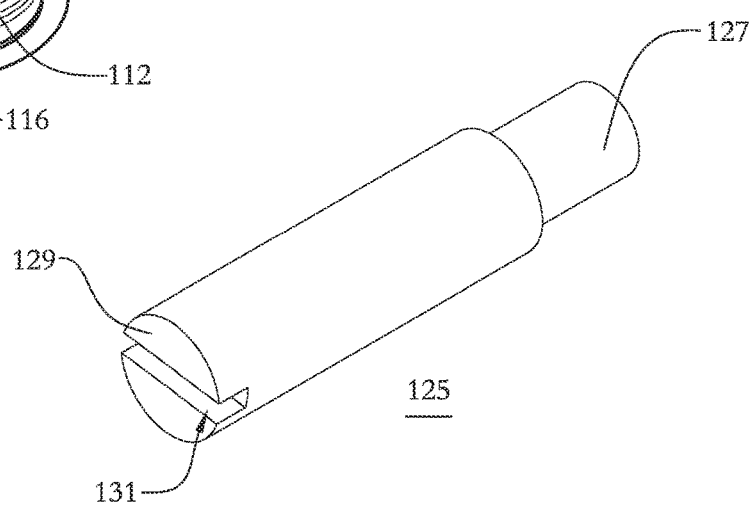
FIG. 17A is perspective view of a component shown in FIG. 1.
Figure 18:
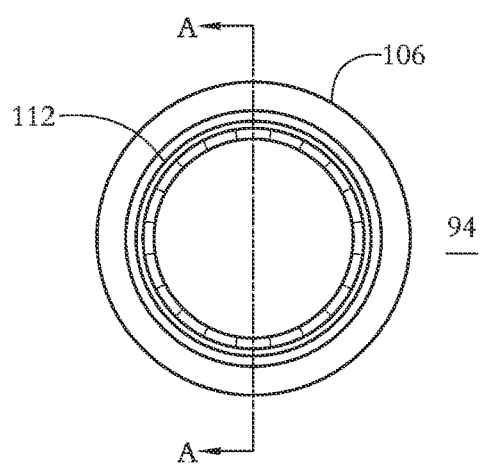
FIG. 18 is an end view of a component shown in FIG. 1.
Figure 19:
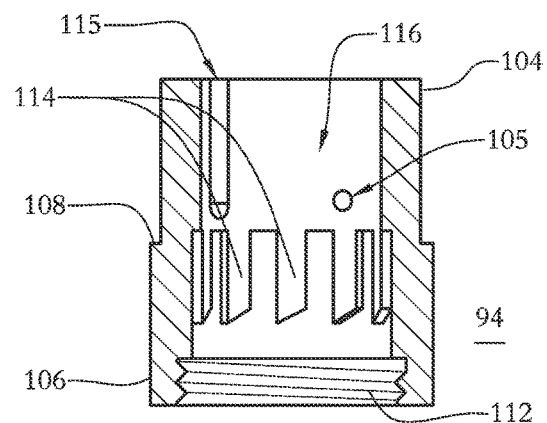
FIG. 19 is a cross sectional view of a component shown in FIG. 1 taken along lines A-A in FIG. 18.
Figures 20, 21:
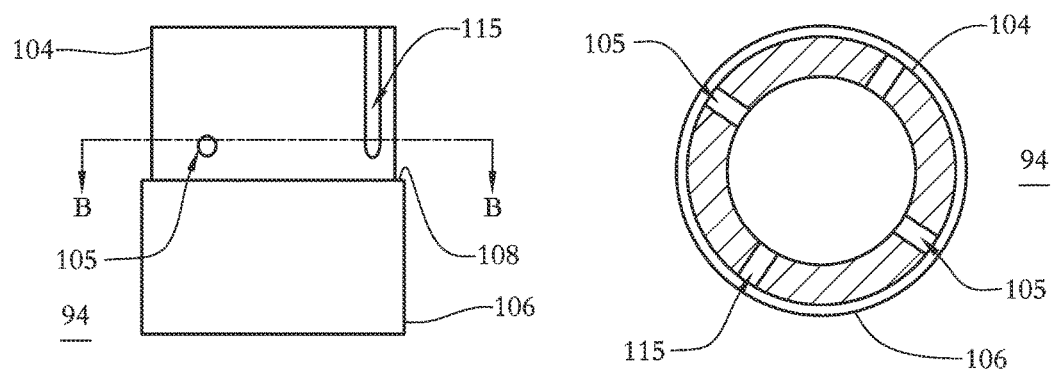
FIG. 20 is a side view of a component shown in FIG. 1.
FIG. 21 is a cross sectional view of a component shown in FIG. 1 taken along lines B-B in FIG. 20.
Figure 22:
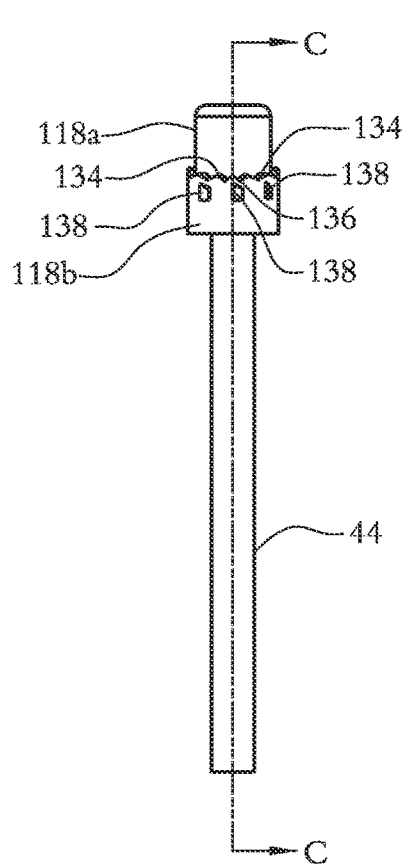
FIG. 22 is a side view of a component shown in FIG. 1.
Figure 23:
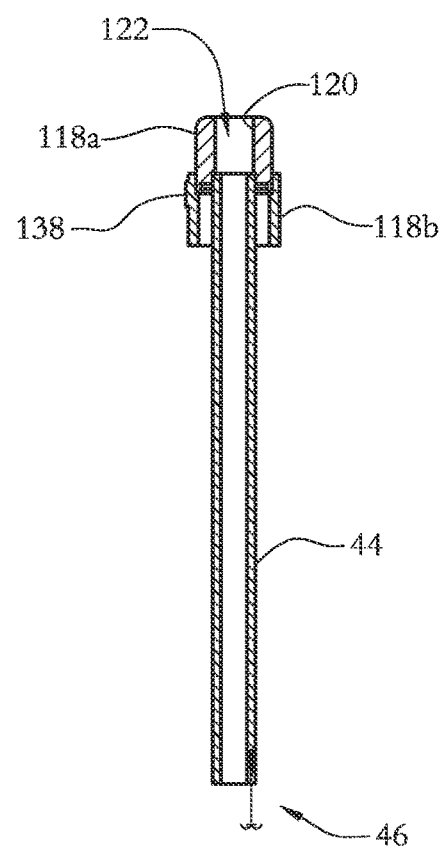
FIG. 23 is a cross sectional view of a component shown in FIG. 1 taken along lines C-C in FIG. 22.
Figures 24, 25:
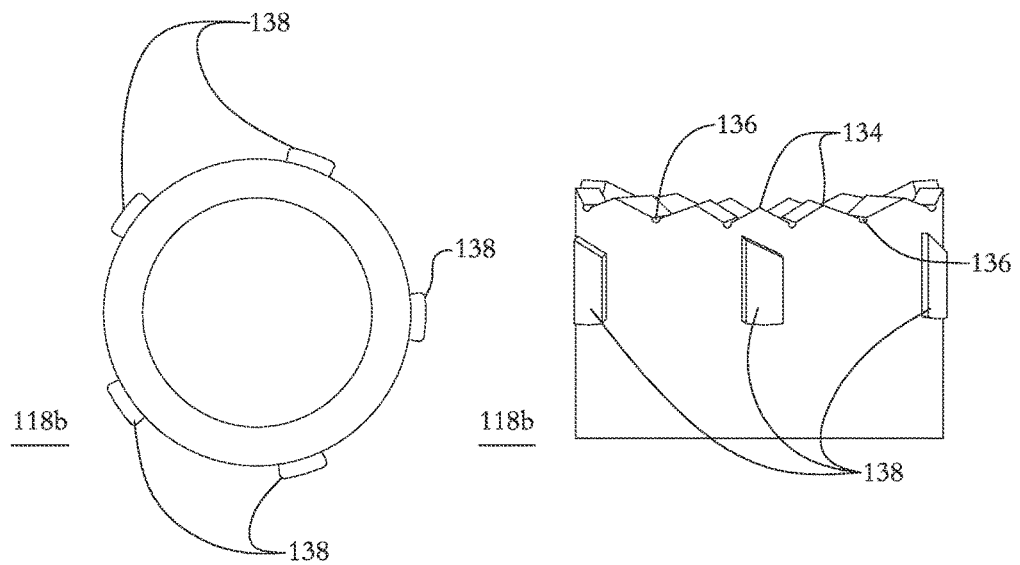
FIG. 24 is an end view of a component shown in FIG. 1.
FIG. 25 is a side view of a component shown in FIG. 1.

In some embodiments, portion 94 comprises one or a plurality of holes 105 extending through inner and outer surfaces of end 104 in a direction that is perpendicular to a longitudinal axis defined by portion 94. Holes 105 each have a cylindrical cross sectional configuration. Holes 105 each have a pin, such as, for example, a rod 125 disposed therein. Rod 125 comprises an end 127 configured for disposal in one of holes 105 and an opposite end 129, as shown in FIG. 17A. In some embodiments, end 129 comprises a tool engagement feature 131 configured for engagement with a tool, such as, for example, a driver and/or actuator to rotate rod 125 about a longitudinal axis defined by rod 125. In some embodiments, end 127 comprises an external thread form configured to engage an internal form of hole 105 to fix rod 125 relative to portion 94. In some embodiments, rods 125 can be variously connected with portion 94, such as, for example, monolithic, integral connection, frictional engagement, threaded engagement, mutual grooves, screws, adhesive, nails, barbs and/or raised element. In some embodiments, portion 94 comprises a pair of holes 105 that are disposed opposite one another such that holes 105 are aligned and/or coaxial, as shown in FIG. 21. In some embodiments, portion 94 comprises a plurality of holes 105 disposed radially about portion 94. Portion 94 further comprises a slot 115 extending parallel to a longitudinal axis defined by portion 94. Slot 115 has a width or diameter greater than that of end 129 such that end 129 can translate within slot 115. Slot 115 includes an arcuate end configured to accommodate the arcuate cross sectional configuration of end 129.

An actuator cutter, such as, for example, an actuator 118 is movably disposed in conduit 116. Actuator 118 comprises a portion 118a and a portion 118b, as shown in FIGS. 22-25. Portion 118b is fixed relative to portion 118a. In some embodiments, portion 118b is integrally and/or monolithically formed with portion 118a. Portion 118b has a diameter that is greater than that of portion 118a. Portion 118a comprises an inner surface 120 defining a channel 122 that is coaxial with axis D. A proximal end of tube 44 is disposed channel 122 such that an outer surface of tube 44 engages surface 120 to fix tube 44 relative to actuator 118. Portion 118b comprises an inner surface 124 defining a chamber 126 having a compression spring, such as, for example, spring 128 disposed therein such that a proximal end 130 of spring 128 engages surface 124 and a distal end 132 of spring 128 is disposed in seat recess 100. This configuration biases actuator 118 in the direction shown by arrow E within body 90. A proximal end of portion 118b comprises a plurality of angled teeth 134. Portion 118b comprises a plurality of concavely curved cutouts 136 positioned between adjacent teeth 134. In some embodiments, cutouts 136 are continuously curved. An outer surface of portion 118b comprises a plurality of spaced apart ridges 138 configured for disposal in grooves 114, as will be discussed. Ridges 138 are disposed radially about portion 118b. In some embodiments, ridges 138 are evenly spaced apart from one another. In some embodiments, proximal ends of ridges 138 are angled to facilitate insertion and/or removal of ridges 138 with grooves 114. In some embodiments, tube 44 can be variously connected with actuator 118, such as, for example, monolithic, integral connection, frictional engagement, threaded engagement, mutual grooves, screws, adhesive, nails, barbs and/or raised element.

Figures 26, 27:
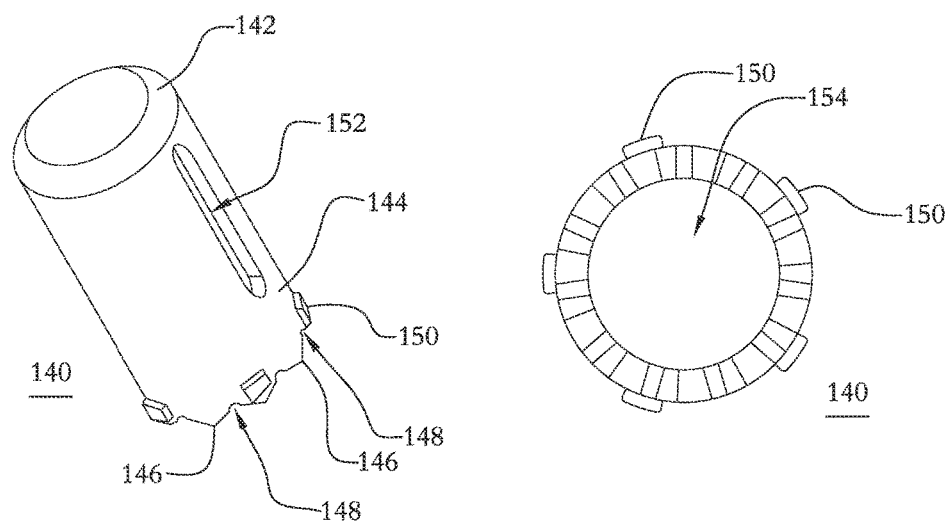
FIG. 26 is perspective view of a component shown in FIG. 1.
FIG. 27 is an end, cross sectional view of a component shown in FIG. 1.

A plug cutter push button, such as, for example, a push button 140 comprises an end 142 extending outside of conduit 116 and an end 144 disposed within conduit 116. End 144 comprises a plurality of angled teeth 146 configured to mate with teeth 134. End 144 comprises a plurality of concavely curved cutouts 148 positioned between adjacent teeth 146, as shown in FIG. 26. In some embodiments, cutouts 148 are continuously curved. An outer surface of push button 140 comprises a plurality of spaced apart ridges 150 disposed in grooves 114 to allow ridges 150 to translate within grooves in the direction shown by arrow E or the direction shown by arrow F. Ridges 150 are positioned radially about push button 140. In some embodiments, ridges 150 are evenly spaced apart from one another. In some embodiments, ridges 150 have a rectangular or square configuration. In some embodiments, ridges 150 are each aligned with one of teeth 146. In some embodiments, device 32 includes the same number of ridges 138 and ridges 150. In some embodiments, device 32 includes the same number of ridges 138, ridges 150 and grooves 114. Push button 140 comprises a slot 152 having an oblong configuration extending parallel to a longitudinal axis defined by push button 140 extending through inner and outer surfaces of push button 140. In some embodiments, slot 152 can have various shape configurations, such as, for example, oval, oblong, polygonal, irregular, uniform, non-uniform, variable and/or tapered. An inner surface of push button 140 defines a channel 154 having a cylindrical cross sectional configuration. An outer surface of actuator 118 engages the inner surface of push button 140 to fix actuator 118 relative to push button 140. Because tube 44 is fixed relative to actuator 118 an actuator is fixed relative to push button 140, tube 44 is axially fixed relative to push button 140 such that moving push button 140 along axis D in the direction shown by arrow E or the direction shown by arrow F also moves tube 44 in the direction shown by arrow E or the direction shown by arrow F. In some embodiments, actuator 118 can be variously connected with push button 140, such as, for example, monolithic, integral connection, frictional engagement, threaded engagement, mutual grooves, screws, adhesive, nails, barbs and/or raised element.

Figure 28:
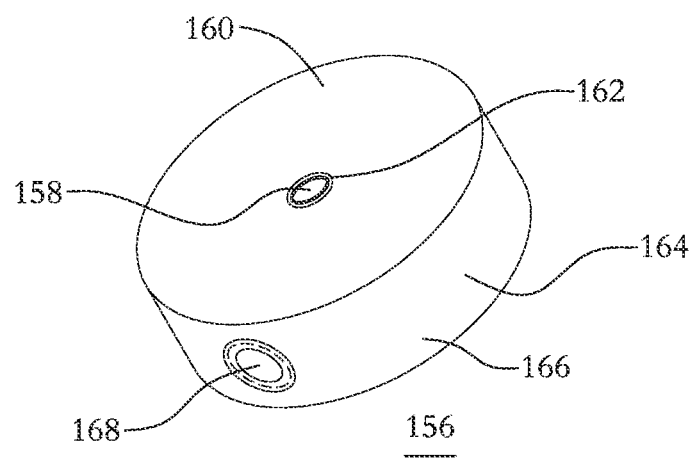
FIG. 28 is perspective view of a component shown in FIG. 1.

An anchor hook guide, such as, for example, a substantially disc-shaped guide member 156 is movably disposed in channel 154. Guide member 156 comprises an inner surface defining a central threaded blind hole 158 extending into a lower surface 160 of guide member 156, as shown in FIG. 28. Hole 158 comprises an internal thread form 162 configured to engage the external thread form on end 74 to fix shaft 72 relative to guide member 156, as shown in FIGS. 2 and 3. Guide member 156 comprises an arcuate outer surface 164 extending between surface 160 and an upper surface 166. Surface 164 is configured to slidingly engage the inner surface of push button 140 that defines channel 154 such that guide member 156 can translate axially within channel 154 in the direction shown by arrow E and the direction shown by arrow F. Surfaces 160, 166 are each planar. Surface 166 extends parallel to surface 160. Guide member 156 comprises a blind hole 168 extending into surface 164. In some embodiments, guide member 156 can be variously connected with shaft 72, such as, for example, monolithic, integral connection, frictional engagement, threaded engagement, mutual grooves, screws, adhesive, nails, barbs and/or raised element.

Figure 29:
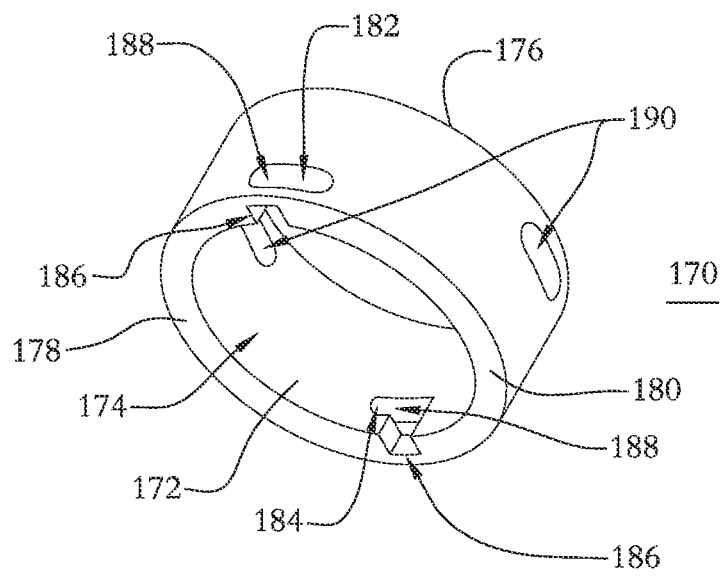
FIG. 29 is perspective view of a component shown in FIG. 1.

A collar 170 is disposed about end 104 such that an inner surface 172 of collar 170 engages an outer surface of end 104. Surface 172 defines a passage 174 having a cylindrical cross sectional configuration, as shown in FIG. 29. Passage 174 has a diameter that is greater than that of end 104 and less than that of end 106 such that collar 170 engages ledge 108 when moved relative to portion 94 in the direction shown by arrow F. Collar 170 extends along a longitudinal axis between an end 176 and an opposite end 178 comprising an end surface 180. Collar 170 comprises a keyway 182 in one portion of collar 170 and a keyway 184 in another portion of collar 170. End 129 of one of rods 125 disposed in holes 105 extends through keyway 182 and end 129 of the other rod 125 disposed in holes 105 extends through keyway 184. Keyways 182, 184 each include a portion 186 extending parallel to the longitudinal axis defined by collar 170 and a portion 188 extending perpendicular to the longitudinal axis defined by collar 170. In some embodiments, portions 186 each extend through surfaces 172, 180 without extending through an outer surface of collar 170 opposite surface 172. In some embodiments, portions 188 extend through surface 172 and the outer surface of collar 170. Portions 186, 188 each have a width or diameter that is greater than that of end 129 such that rods 125 can move within portions 186, 188, as will be discussed. In some embodiments, keyway 182 is disposed opposite keyway 184 such that keyway 182 is disposed 180 degrees from keyway 184. In some embodiments, portions 188 each have an arcuate end portion configured to accommodate the arcuate configuration of end 129. Collar 170 further includes spaced apart oblong openings 190 extending perpendicular to the longitudinal axis defined by collar 170. Openings 190 extend through surface 172 and the outer surface of collar 170. In some embodiments, collar 170 includes a single opening 190. In some embodiments, opening 190 can have various shape configurations, such as, for example, oval, oblong, polygonal, irregular, uniform, non-uniform, variable and/or tapered. A pin, such as, for example, rod 125 is positioned relative to guide member 156 such that end 127 is positioned in hole 168 and end 129 extends through slots 115, 152 for disposal in opening 190. Opening 190 has a height that is substantially equivalent to the width or diameter of end 129 such that end 129 is prevented from moving in the direction shown by arrow E or the direction shown by arrow F within opening 190. Because shaft 72 is fixed to guide member 156, shaft 72 is axially fixed relative to collar 170. That is, as collar 170 moves along axis D in the direction shown by arrow E or the direction shown by arrow F, so does shaft 72.

Push button 140 is pressed once in the direction shown by arrow F, causing ridges 150 translate within grooves 114 in the direction shown by arrow F such that actuator 118 translates within portions 92, 94 in the direction shown by arrow F. As actuator 118 translates within portions 92, 94 in the direction shown by arrow F, cutting element 48 moves away from an end surface 45 of tube 34 in the direction shown by arrow F. When push button 140 is pressed, cutting element 84 extends further from end surface 45 than does cutting element 48. In some embodiments, the distance push button 140 is moved in the direction shown by arrow F is less than the distance cutting element 48 moves away from end surface 45. In some embodiments, the distance push button 140 is moved in the direction shown by arrow F is equal to the distance cutting element 48 moves away from end surface 45. In some embodiments, the distance push button 140 is moved in the direction shown by arrow F is greater than the distance cutting element 48 moves away from end surface 45. In some embodiments, cutting element 84 extends an equal distance from end surface 45 as cutting element 48 when push button 140 is pressed. In some embodiments, cutting element 48 extends further from end surface 45 than does cutting element 84.

As push button 140 translates within portions 92, 94 in the direction shown by arrow F, teeth 146 engage teeth 134. Due to the force applied to portion 118b by spring 128 and/or the angled configurations of teeth 134, 146, portion 118b rotates relative to push button 140 and/or portion 94 as teeth 134 engage teeth 146. Because ridges 150 are positioned in grooves 114, push button 140 does not rotate relative to portion 94 as portion 118b rotates relative to portion 94. In that shaft 72 is fixed relative to portion 118b, rotating portion 118b also rotates shaft 72 and cutting element 48 about axis D. In some embodiments, pressing push button 140 once in the direction shown by arrow F causes portion 118b to rotate relative to push button 140 a first amount. In some embodiments, the first amount is between about 10 and about 100 degrees. In some embodiments, the first amount is between about 30 and about 80 degrees. In some embodiments, the first amount is between about 40 and about 70 degrees. In some embodiments, the first amount is between about 50 and about 60 degrees. In some embodiments, the first amount is about 60 degrees.

When push button 140 is pressed once in the direction shown by arrow F, portion 118b rotates relative to portions 92, 94 such that extensions 138 are aligned with grooves 114. As such, when the force used to press push button 140 once is removed, portion 118b moves relative to portions 92, 94 in the direction shown by arrow F. As portion 118b moves relative to portions 92, 94 in the direction shown by arrow F, extensions 138 move into grooves 114 and translate relative to portions 92, 94 in the direction shown by arrow E. In some embodiments, the angled configuration of the top portions of extensions 138 urges extensions 138 into grooves 114 as portion 118b moves relative to portions 92, 94 in the direction shown by arrow E. This configuration requires that push button 140 be pressed down to overcome the force exerted by spring 128 to move cutting element 48 away from end surface 45 in the direction shown by arrow F. Indeed, once the force used to press push button 140 down is removed, cutting element 48 moves toward end surface 45 in the direction shown by arrow E, as discussed above. This feature prevents device 32 from being locked or otherwise fixed in a position such that cutting element 48 extends beyond its initial position relative to end surface 45.

Pressing push button 140 a second time causes portion 118b to move relative to portions 92, 94 in the direction shown by arrow F such that cutting element 48 moves away from end surface 45 in the direction shown by arrow F, as described above when push button 140 is pressed once. As such, push button 140 may be pressed any number of times to move cutting element 48 away from end surface 45 in the direction shown by arrow F a corresponding number of times. Pressing push button 140 a second time also causes portion 118b to rotate relative to push button 140 a second amount that is equal to the first amount, as described above, when push button 140 is pressed once. As such, depending upon the degree of rotation provided by the first amount, push button 140 may be pressed a number of times to move cutting element 48 three hundred and sixty degrees about axis D.

Collar 170 is positioned relative to portion 94 such that ends 129 of the rods 125 positioned in holes 105 are positioned in portions 188 of keyways 182, 184. This configuration prevents collar 170 from translating relative to portion 94 in the direction shown by arrow F. Collar 170 is rotated relative to portion 94 about axis D in a first direction, such as, for example, clockwise or counterclockwise, to move ends 129 of the rods 125 positioned in holes 105 from portions 188 of keyways 182, 184 and into portions 186 of keyways 182, 184, thus allowing collar 170 to translate relative to portion 94 in the direction shown by arrow E. Collar 170 is translated along axis D in the direction shown by arrow E such that guide member 156 also translates in the direction shown by arrow E. As guide member 156 also translates in the direction shown by arrow E, cutting member 84 translates in the direction shown by arrow E. The maximum distance cutting member 84 can translate along axis D in the direction shown by arrow E is limited by the length of slot 152. In some embodiments, slot 152 has a length that permits cutting member 84 to be translated along axis D in the direction shown by arrow E until cutting member 84 is disposed entirely within passageway 42.

In assembly, operation and use, system 30 is employed with a surgical procedure, such as, for a treatment of a hypertrophied ligamentum flavum. It is contemplated that one or all of the components of system 30 can be delivered or implanted as a pre-assembled device or can be assembled in situ. System 30 may be completely or partially revised, removed or replaced. It is envisioned that system 30 may also be used to treat other affected portions of the patient, such as, for example, a calcaneus bone, bones of the feet or hands, bones of the spine, bones of the arms and legs, etc.

In use, to treat a hypertrophied ligamentum flavum, a medical practitioner obtains access to a surgical site including in any appropriate manner, such as through the skin, or through an incision and retraction of tissues. In one embodiment, a drill is employed to remove bone tissue to provide access to a repair site. It is envisioned that system 30 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 30 is determined according to the configuration, dimension and location of a selected section of nerves and the requirements of a particular application.

An incision is made in the body of a patient and a cutting instrument (not shown) creates a surgical pathway for implantation of components of system 30. This may include the use of a cannula or other device. A preparation instrument (not shown) can be employed to prepare tissue surfaces, as well as for aspiration and irrigation of a surgical region according to the requirements of a particular surgical application.

Device 32 is inserted into the surgical site, such as, for example adjacent a ligamentum flavum. In some embodiments, device 32 is positioned adjacent the ligamentum flavum such that cutting member 84 engages the ligamentum flavum and cutting element 48 is spaced apart from the ligamentum flavum. In some embodiments, engaging cutting element 84 with the ligamentum flavum comprises positioning cutting element 84 such that cutting element 84 penetrates the ligamentum flavum. In some embodiments, engaging cutting element 84 with the ligamentum flavum comprises positioning cutting element 84 such that a portion of the ligamentum flavum is positioned within a hook portion of the ligamentum flavum.

Push button 140 is pressed once, as described above, to move cutting element 48 away from end surface 45 in the direction shown by arrow F. As cutting element 48 moves away from end surface 45 in the direction shown by arrow F, cutting element 48 penetrates the ligamentum flavum. As discussed above, cutting element 48 also rotates about axis D when push button 140 is pressed. As such, cutting element 48 rotates about axis D as cutting element 48 moves away from end surface 45 in the direction shown by arrow F such that cutting element 48 penetrates the ligamentum flavum as cutting element 48 rotates about axis D and simultaneously penetrates the ligamentum flavum as cutting element 48 moves away from end surface 45 in the direction shown by arrow F. When push button 140 is released, portion 118b moves relative to portions 92, 94 in the direction shown by arrow E such that cutting element 48 translates in the direction shown by arrow E. As cutting element 48 translates in the direction shown by arrow E, cutting element 48 cuts through the ligamentum flavum. Push button 140 may be pressed a selected number of times to rotate cutting element 48 a selected amount about axis D.

In some embodiments, cutting element 48 is rotated three hundred and sixty degrees about axis D such that cutting element 48 cuts a substantially circular and/or disc shaped portion of the ligamentum flavum. However, it should be understood that the shape, size, etc. of the portion of the ligamentum flavum that is to be removed from the remaining portion of the ligamentum flavum may have any configuration selected by the medical practitioner, and hence need not be substantially circular and/or disc shaped. For clarity, the portion of the ligamentum flavum that is removed from the remaining portion of the ligamentum flavum will be referred to as the substantially circular and/or disc shaped portion of the ligamentum flavum. In some embodiments, the disc shaped portion of the ligamentum flavum is removable from a remaining portion of the ligamentum flavum. That is, there is no tissue or otherwise connecting the disc shaped portion of the ligamentum flavum with the remaining portion of the ligamentum flavum that may prevent the disc shaped portion of the ligamentum flavum from being removed from the remaining portion of the ligamentum flavum. In some embodiments, cutting element 48 is rotated less than three hundred and sixty degrees about axis D. In some embodiments, cutting element 48 is rotated more than three hundred and sixty degrees about axis D to ensure that the disc shaped portion of the ligamentum flavum is removable from a remaining portion of the ligamentum flavum. As discussed above, the number of times push button 140 needs to be pressed in order to rotate cutting element 48 about axis D the selected amount is dependent upon the amount pressing push button 140 once rotates cutting element 48 about axis D. In some embodiments, a medical practitioner may press push button 140 between 5 and 50 times to rotate cutting element 48 three hundred and sixty degrees about axis D.

Collar 170 is positioned relative to portion 94 such that ends 129 of the rods 125 positioned in holes 105 are positioned in portions 188 of keyways 182, 184. This configuration prevents collar 170 from translating relative to portion 94 in the direction shown by arrow F. Collar 170 is rotated relative to portion 94 about axis D in a first direction, such as, for example, clockwise or counterclockwise, to move ends 129 of the rods 125 positioned in holes 105 from portions 188 of keyways 182, 184 and into portions 186 of keyways 182, 184, thus allowing collar 170 to translate relative to portion 94 in the direction shown by arrow E. Collar 170 is translated along axis D in the direction shown by arrow E such that guide member 156 also translates in the direction shown by arrow E. As guide member 156 translates in the direction shown by arrow E, cutting member 84 translates in the direction shown by arrow E such that cutting element 84 pulls the disc shaped portion of the ligamentum flavum away from the remaining portion of the ligamentum flavum.

Upon completion of the surgical procedure, device 32 is removed from the surgical site. It is envisioned that the use of microsurgical and image guided technologies may be employed to access, view and repair spinal deterioration or damage, with the aid of device 32. It is contemplated that a surgical procedure may employ other instruments that can be mounted with device 32, such as, for example, nerve root retractors, tissue retractors, forceps, cutter, drills, scrapers, reamers, rongeurs, taps, cauterization instruments, irrigation and/or aspiration instruments, illumination instruments, inserter instruments and/or separators, such as, for example, one or more burrs. Device 32 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A cutting device comprising:
   an outer tube extending along a longitudinal axis between a proximal end and a distal end, the outer tube comprising an inner surface defining a passageway;
   an inner tube movably disposed in the passageway such that a distal end of the inner tube extends beyond the distal end of the outer tube, the distal end of the inner tube comprising a first cutting element comprising a plurality of tines in a tine arrangement, and an inner surface of the inner tube defining a lumen;
   a shaft slidably disposed in the lumen, the shaft comprising a distal end including a second cutting element comprising a stylet that protrudes distally from a center of the tine arrangement; and
   a deployment mechanism coupled to the proximal end of the outer tube and comprising a body, a push button disposed within the body and a collar disposed about the body, the shaft being axially fixed relative to the collar and the inner tube being axially fixed relative to the push button.

2. A cutting device as recited in claim 1, wherein a proximal end of the shaft is coupled to a guide member slidably positioned within the push button, the guide member comprising a pin extending through a slot in the push button and a slot in the body, the pin being axially fixed relative to the collar.

3. A cutting device as recited in claim 1, wherein the shaft is movable between a first configuration in which the second cutting element is disposed within the passageway and a second configuration in which the second cutting element is positioned outside of the passageway.

4. A cutting device as recited in claim 3, wherein the shaft moves between the first and second configurations by translating the collar relative to the body along the longitudinal axis.

5. A cutting device as recited in claim 4, wherein the shaft is locked in the second configuration by rotating the collar about the body.

6. A cutting device as recited in claim 1, wherein the push button comprises a distal end comprising a plurality of teeth, the teeth being configured to engage teeth on a proximal end of an actuator movably disposed within the body, the inner tube being fixed relative to the actuator, the deployment mechanism comprising a spring positioned between the body and a distal end of the actuator.

7. A cutting device as recited in claim 6, wherein:
   the spring biases the actuator toward the push button such that moving the push button distally relative to the body causes the teeth on the push button to engage the teeth on the actuator such that the actuator rotates relative to the push button about the longitudinal axis; and
   the inner tube rotates relative to the outer tube about the longitudinal axis as the actuator rotates relative to the push button about the longitudinal axis.

8. A cutting device as recited in claim 7, wherein moving the push button distally relative to the body moves the first cutting element between a first orientation in which the first cutting element has a first radial position relative to the outer tube and a second orientation in which the first cutting element has a second radial position relative to the outer tube that is different than the first radial position.

9. A cutting device as recited in claim 7, wherein:
   an inner surface of the body includes a plurality of spaced apart grooves;
   an outer surface of the actuator comprises a plurality of projections; and
   the push button is movable relative to the body between a first configuration in which the projections are spaced apart from the grooves and the actuator is prevented from moving proximally relative to the body and a second configuration in which the projections are disposed in the grooves and the actuator moves proximally relative to the body.

10. A cutting device as recited in claim 1, wherein the inner tube including the first cutting element is offset from the longitudinal axis and the shaft including the second cutting element is coaxial with the longitudinal axis.

11. A cutting device as recited in claim 1, wherein the tines are evenly spaced apart from one another.

12. A cutting device as recited in claim 1, wherein the tines are evenly spaced apart from one another at angles of about 45 degrees.

13. A cutting device as recited in claim 1, wherein the second cutting element is defined by a single hook.

14. A cutting device comprising:
   an outer tube extending along a longitudinal axis between a proximal end and a distal end, the outer tube comprising an inner surface defining a passageway;
   an inner tube movably disposed in the passageway such that a distal end of the inner tube extends beyond the distal end of the outer tube, the distal end of the inner tube comprising a first cutting element including a plurality of tines in a tine arrangement, and an inner surface of the inner tube defining a lumen;
   a shaft slidably disposed in the lumen, the shaft comprising a distal end including a second cutting element comprisinq a stylet that protrudes distally from a center of the tine arrangement; and
   a deployment mechanism coupled to the proximal end of the outer tube and comprising a body, a push button disposed within the body and a collar disposed about the body, the shaft including the second cutting element being axially fixed relative to the collar and the inner tube being axially fixed relative to the push buttons,
   wherein the shaft including the second cutting element is movable between a first configuration in which the second cutting element is disposed within the lumen and a second configuration in which the second cutting element is positioned outside of the lumen by translating the collar relative to the body along the longitudinal axis, and wherein moving the push button distally relative to the body moves the first cutting element between a first orientation in which the first cutting element has a first radial position relative to the outer tube and a second orientation in which the first cutting element has a second radial position relative to the outer tube that is different than the first radial position.

15. A cutting device as recited in claim 14, wherein a proximal end of the shaft is coupled to a guide member slidably positioned within the push button, the guide member comprising a pin extending through a slot in the push button and a slot in the body, the pin being axially fixed relative to the collar.

16. A cutting device as recited in claim 14, wherein the push button comprises a distal end comprising a plurality of teeth, the teeth being configured to engage teeth on a proximal end of an actuator movably disposed within the body, the inner tube being fixed relative to the actuator, the deployment mechanism comprising a spring positioned between the body and a distal end of the actuator.

17. A cutting device comprising:
- an outer tube extending along a longitudinal axis between a proximal end and a distal end, the outer tube comprising an inner surface defining a passageway;
- an inner tube movably disposed in the passageway such that a distal end of the inner tube extends beyond the distal end of the outer tube, the distal end of the inner tube comprising a first cutting element, and an inner surface of the inner tube defining a lumen;
- a shaft slidably disposed in the lumen, the shaft comprising a distal end including a second cutting element; and
- a deployment mechanism coupled to the proximal end of the outer tube and comprising a body, a push button disposed within the body, and a collar disposed about the body, the shaft being axially fixed relative to the collar and the inner tube being axially fixed relative to the push button, the push button comprising a distal end comprising a plurality of teeth, the teeth being configured to engage teeth on a proximal end of an actuator movably disposed within the body, the inner tube being fixed relative to the actuator, and the deployment mechanism comprising a spring positioned between the body and a distal end of the actuator.

18. A cutting device as recited in claim 17, wherein:
- the spring biases the actuator toward the push button such that moving the push button distally relative to the body causes the teeth on the push button to engage the teeth on the actuator such that the actuator rotates relative to the push button about the longitudinal axis; and
- the inner tube rotates relative to the outer tube about the longitudinal axis as the actuator rotates relative to the push button about the longitudinal axis.

19. A cutting device as recited in claim 18, wherein moving the push button distally relative to the body moves the first cutting element between a first orientation in which the first cutting element has a first radial position relative to the outer tube and a second orientation in which the first cutting element has a second radial position relative to the outer tube that is different than the first radial position.

20. A cutting device as recited in claim 18, wherein:
- an inner surface of the body includes a plurality of spaced apart grooves;
- an outer surface of the actuator comprises a plurality of projections; and
- the push button is movable relative to the body between a first configuration in which the projections are spaced apart from the grooves and the actuator is prevented from moving proximally relative to the body and a second configuration in which the projections are disposed in the grooves and the actuator moves proximally relative to the body.

\* \* \* \* \*

UNITED STATES PATENT AND TRADEMARK OFFICE
CERTIFICATE OF CORRECTION

PATENT NO. : 9,968,370 B2
APPLICATION NO. : 14/288508
DATED : May 15, 2018
INVENTOR(S) : Goshayeshgar Page 1 of 1

It is certified that error appears in the above-identified patent and that said Letters Patent is hereby corrected as shown below:

In the Drawings

Figure 5:
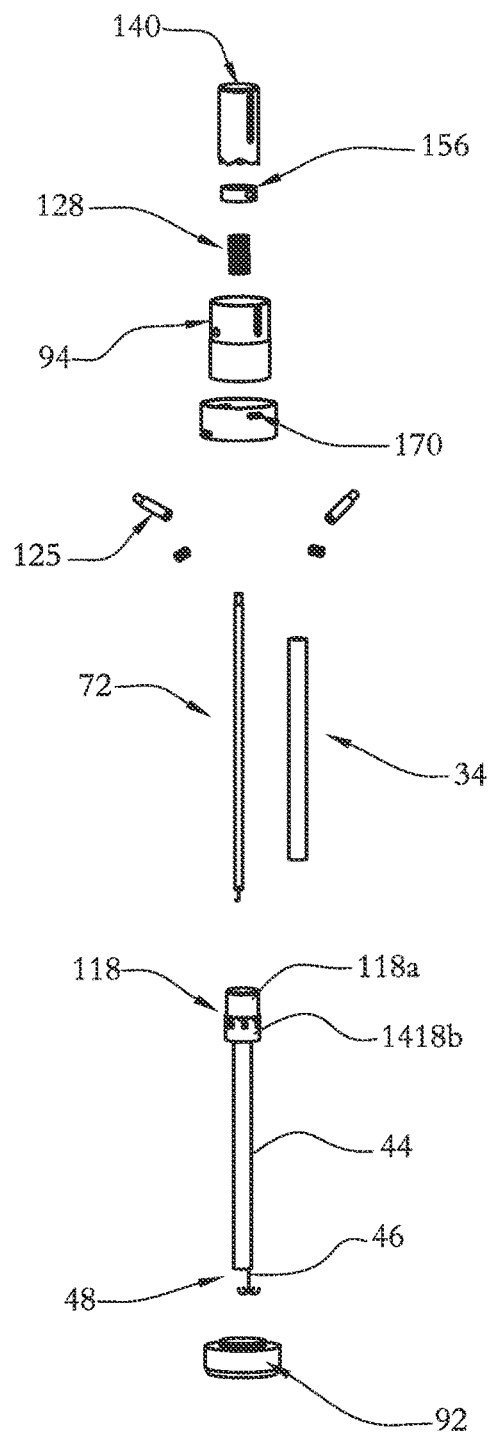
FIG. 5 is a side view of components shown in FIG. 1, with parts separated.

In Fig. 5, Sheet 3 of 11, delete Tag "1418b" and insert Tag -- 118b --, therefor.

In the Specification

In Column 2, Line 59, delete "so" and insert -- of --, therefor.

In Column 7, Line 23, delete "cavity 48," and insert -- cavity 58, --, therefor.

In Column 7, Line 27, delete "cavity 48" and insert -- cavity 58 --, therefor.

In Column 7, Line 30, delete "cavity 48." and insert -- cavity 58. --, therefor.

In Column 7, Line 45, delete "tines 46" and insert -- tines 50 --, therefor.

In the Claims

In Column 16, Line 56, in Claim 14, delete "comprisinq" and insert -- comprising --, therefor.

In Column 16, Line 63, in Claim 14, delete "buttons," and insert -- button, --, therefor.

Signed and Sealed this
Thirtieth Day of October, 2018

Andrei Iancu
*Director of the United States Patent and Trademark Office*